United States Patent
Deshpande et al.

(10) Patent No.: US 9,849,151 B2
(45) Date of Patent: Dec. 26, 2017

(54) SALACIA COMPOSITIONS, METHODS OF TREATMENT BY THEIR ADMINISTRATION, AND METHODS OF THEIR PREPARATION

(71) Applicant: OmniActive Health Technologies (Canada) Limited, Charlottetown (CA)

(72) Inventors: Jayant Deshpande, Charlottetown (CA); Khadija Ghanam, Charlottetown (CA); Stephen Ewart, Charlottetown (CA); Vijaya Juturu, Morristown, NJ (US)

(73) Assignee: OmniActive Health Technologies (Canada) Limited, Charlottetown (CA)

( * ) Notice: Subject to any disclaimer, the term of this patent is extended or adjusted under 35 U.S.C. 154(b) by 0 days.

(21) Appl. No.: 14/547,537

(22) Filed: Nov. 19, 2014

(65) Prior Publication Data

US 2015/0141355 A1   May 21, 2015

Related U.S. Application Data

(60) Provisional application No. 61/906,194, filed on Nov. 19, 2013.

(51) Int. Cl.

| | | |
|---|---|---|
| *A61K 36/37* | (2006.01) | |
| *A61K 31/122* | (2006.01) | |
| *A61K 31/192* | (2006.01) | |
| *A61K 31/7048* | (2006.01) | |
| *A23L 33/10* | (2016.01) | |
| *A23L 33/105* | (2016.01) | |

(52) U.S. Cl.
CPC .............. *A61K 36/37* (2013.01); *A23L 33/10* (2016.08); *A23L 33/105* (2016.08); *A61K 31/122* (2013.01); *A61K 31/192* (2013.01); *A61K 31/7048* (2013.01)

(58) Field of Classification Search
CPC .. A61K 36/37; A61K 31/7048; A61K 31/122; A61K 31/192
USPC .......................................................... 514/27
See application file for complete search history.

(56) References Cited

U.S. PATENT DOCUMENTS

| | | |
|---|---|---|
| 7,553,502 B2 | 6/2009 | Bombardelli et al. |
| 8,114,445 B2 | 2/2012 | Hastings |
| 8,241,677 B2 | 8/2012 | Ueda et al. |
| 8,337,911 B2 | 12/2012 | Dubey et al. |
| 8,420,131 B2 | 4/2013 | Smith |
| 2002/0004190 A1 | 1/2002 | Diasti et al. |
| 2007/0037870 A1 | 2/2007 | Asada et al. |
| 2008/0102144 A1 | 5/2008 | Clement et al. |
| 2008/0220098 A1 | 9/2008 | Bombardelli et al. |
| 2008/0241292 A1 | 10/2008 | Heuer et al. |
| 2009/0263505 A1 | 10/2009 | Hammons |
| 2010/0247501 A1 | 9/2010 | Ikeda |
| 2011/0236488 A1 | 9/2011 | Krishnan |
| 2012/0100248 A1 | 4/2012 | Das et al. |
| 2012/0276081 A1 | 11/2012 | Oda et al. |
| 2014/0186466 A1 | 7/2014 | Patel |

FOREIGN PATENT DOCUMENTS

| | | |
|---|---|---|
| EP | 2 397 039 | 12/2011 |
| EP | 2 054 070 | 8/2013 |
| JP | 04103536 | 4/1992 |
| JP | 2002267655 | 9/2002 |
| JP | 2010043035 | * 2/2010 |
| JP | 2013107854 | 6/2013 |
| WO | WO 2001/072316 | 10/2001 |
| WO | 2008049198 | 5/2008 |
| WO | WO 2008/136013 | 11/2008 |
| WO | WO 2008/142702 | 11/2008 |
| WO | WO 2012/024270 | 2/2012 |
| WO | WO 2013/016742 | 1/2013 |
| WO | 2013150771 | 10/2013 |

OTHER PUBLICATIONS

Pinelo et al. Effect of Solvent, Temperature, and Solvent-to-Solid Ratio on the Total Phenolic Content and Antiradical Activity of Extracts from Different Components of Grape Pomace. J. Agric. Food Chem. 53:2111-2117, 2005.*
Anu et al. New norfriedelene-1,3-dione from the root bark of Salacia oblonga. Indian Journal of Chemistry vol. 42B, May 2003, pp. 1180-1182.*
Chawla et al. Salacia oblonga Wall: A Review on its Pharmacognostic, Phytochemical and Pharmacological Aspects. International Journal of Research in Pharmaceutical and Biomedical Sciences vol. 4 (4): 1215-1228, Oct.-Dec. 2013.*
Anu. S. J. Chemical Investigations on Some Medicinal Plants Used in Diabetes. Thesis, the University of Kerala. Organic Chemistry Division Regional Research Laboratory Thiruvananthapuram-695 019. Kerala. India. May 2000 (Year: 2000).*
Li et al., "*Salacia oblonga* improves cardiac fibrosis and inhibits postprandial hyperglycemia in obese zucker rats", Life Sciences, vol. 75, pp. 1735-1746, 2004.
Yoshikawa et al., "Biological Activities of *Salacia chinensis* Originating in Thailand: The Quality Evaluation Guided by α-Glucosidase Inhibitory Activity", Yakugaku Zasshi, The Pharmaceutical Society of Japan, vol. 123(10), pp. 871-880, 2003.

(Continued)

*Primary Examiner* — Yih-Horng Shiao
(74) *Attorney, Agent, or Firm* — Hamre, Schumann, Mueller & Larson, P.C.

(57) ABSTRACT

A *Salacia* composition described herein significantly reduces appetite, activates Hormone Sensitive Lipase, and manages a healthy lipid profile through inhibition of HMG-CoA Reductase enzyme. *Salacia* compositions described herein include of at least 12% of polyphenols, 2% of mangiferin and 1% of 25,26-oxidofriedelane-1,3-dione by weight of the composition in the form of extract. The composition is obtained by continuous solvent extraction, employing non-aqueous food grade solvents. *Salacia* compositions herein reduce appetite by about 18% of routine diet, when effective amounts are administered to a subject in need thereof. Effective management of a healthy lipid profile is thus possible with synergistic combination of reduction in energy intake, activation of Hormone Sensitive Lipase, and inhibition of HMG-CoA Reductase enzyme responsible for cholesterol metabolism.

18 Claims, 2 Drawing Sheets

(56) References Cited

OTHER PUBLICATIONS

Im et al., "Aqueous Extract of Kotahla Himbutu (*Salacia reticulata*) Stems Promotes Oxygen Comsumption and Supresses Body Fat Accumulation in Mice", Journal of Health Science, vol. 54(6), pp. 645-653, 2008.

Serasinghe et al., "Oral Hypoglycemic Effect of *Salacia reticulata* in the Streptozotocin Induced Diabetic Rat", Phototherapy Research, vol. 4, No. 5, pp. 205-206, 1990.

Yoshikawa et al., "Absolute Stereostructure of Potent α-Glucosidase Inhibitor, Salacinol, with Unique Thiosugar Sulfonium Sulfate Inner Salt Structure from *Salacia reticulate*", Bioorganic & Medicinal Chemistry, vol. 10, pp. 1547-1554, 2002.

Yoshikawa et al., "*Salacia reticulata* and Its Polyphenolic Constituents with Lipase Inhibitory and Lipolytic Activities Have Mild Antiobesity Effects in Rats", The Journal of Nutrition, American Society for Nutritional Sciences, pp. 1819-1824, 2002.

International Search Report and Written Opinion issued in the corresponding International Application No. PCT/IB2014/002990, dated May 12, 2015.

Sikarwar et al., "Antihyperlipidemic activity of Salacia chinensis root extracts in triton-induced and atherogenic diet-induced hyperlipidemic rats", Indian Journal of Pharmacology, Feb. 2012, vol. 44, No. 1, pp. 88-92.

Koga et al., "Proanthocyanidin Oligomers Isolated From Salacia reticulata Leaves Potently Inhibit Pancreatic Lipase Activity", Journal of Food Science, Jan. 2013, vol. 78, No. 1, 8 pages.

Huang et al., "Salacia oblonga root improves postprandial hyperlipidemia and hepatic steatosis in Zucker diabetic fatty rats: Activation of PPAR-α", Toxicology and Applied Pharmacology, 2006, vol. 210, pp. 225-235.

Extended European Search Report and Written Opinion, issued in the corresponding European patent application No. 14864855.3, dated Aug. 8, 2017, 14 pages.

\* cited by examiner

Figure 1: HPTLC Fingerprint images of Salacia composition
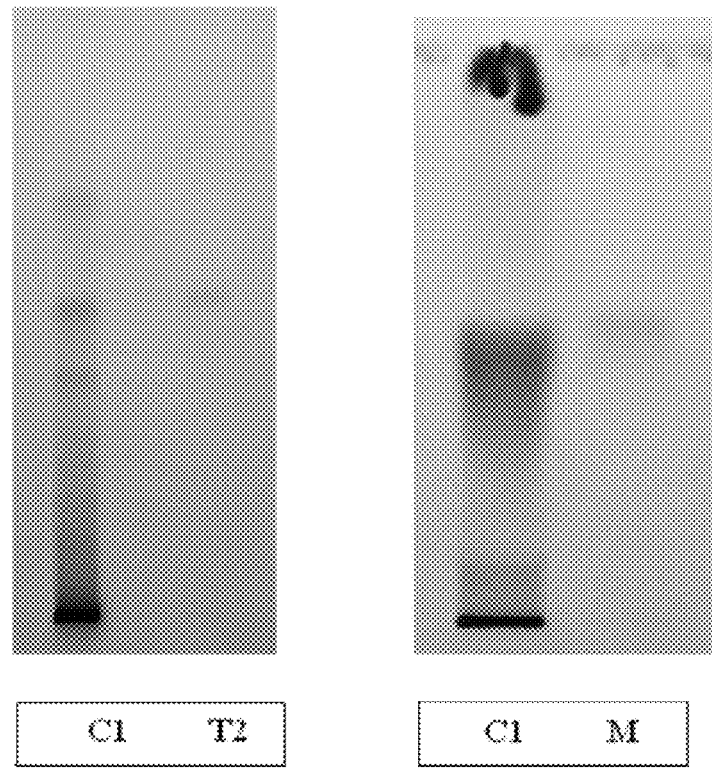
C1- Salacia composition
T2- 25,26-oxidofriedelane-1,3-dione
M- mangiferin
Figure 2: Effect of Salacia composition on pancreatic lipase
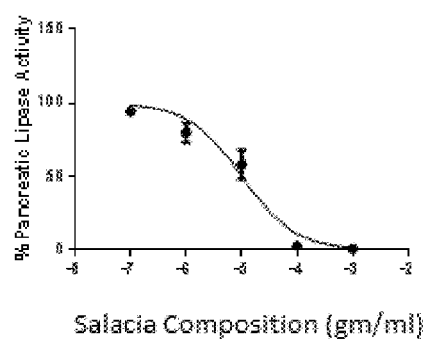

Figure 3: Effect of Salacia composition on alpha-glucosidase enzyme
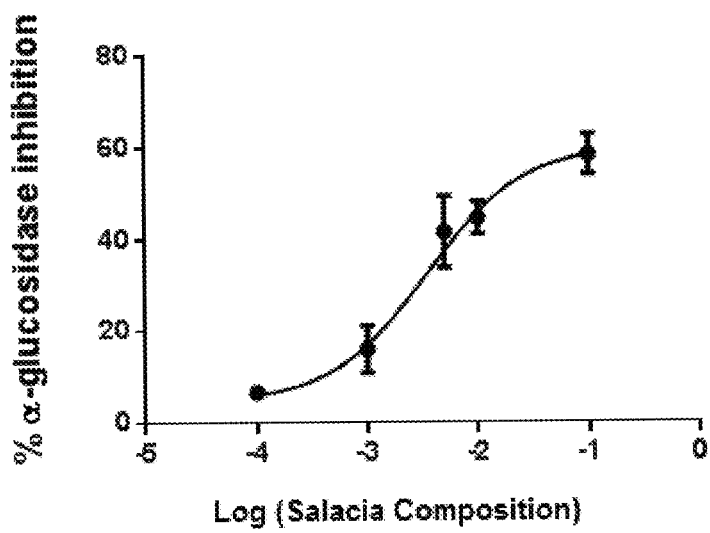

SALACIA COMPOSITIONS, METHODS OF TREATMENT BY THEIR ADMINISTRATION, AND METHODS OF THEIR PREPARATION

FIELD

*Salacia* compositions, methods of their preparation, and methods of treatment by their use are described, and that significantly reduces appetite, activates Hormone Sensitive Lipase and manages healthy lipid profile through inhibition of HMG-CoA Reductase enzyme. *Salacia* composition described herein include at least 12% of polyphenols, 2% of mangiferin and 1% of 25,26-oxidofriedelane-1,3-dione by weight of the composition in the form of extract. The composition is prepared by using non-aqueous food grade solvents and significantly reduces the appetite, when administered in effective amounts, to an individual in need thereof. *Salacia* composition manages healthy lipid profile by inhibiting HMG-CoA Reductase enzyme and activating Hormone Sensitive Lipase. Novel *Salacia* compositions herein are safe for human consumption, prepared by economic process using conventional equipments, and useful for managing a healthy lipid profile by regulating enzymes involved in lipid metabolism.

BACKGROUND

Imbalance between energy intake and expenditure results in excessive weight gain of an individual, followed by dyslipidemia and cardiovascular diseases in young adults. Energy intake is directly co-related with food consumption and when food is consumed in more amount than body requirement, balance of energy utilization is disturbed. A high rate of morbidity and early mortality is evident due to obesity and is widely recognized as the largest and fastest growing medical and public health problems in the developed and developing world. Prevalence of this disorder in adults has more than tripled in the past decade, and it currently affects approximately 30-35% of the general population in the USA and 25% in the UK. The relation between obesity and disease risk begins early in life and the survey indicates that individuals suffering from obesity and disturbed lipid profile are also associated with high blood pressure and fatty deposits in coronary arteries. Major comorbidities thus include type 2 diabetes, metabolic syndrome, hypertension, dyslipidaemia, myocardial infarction, stroke, certain cancers, sleep apnea and osteoarthritis. These observations are likely to reflect national trends and certainly deserve a sharper focus for timely treatment of such individuals to prevent further weight gain or reduce weight and manage lipid profile.

Although prevention through education and changes to the obesogenic environment are long-term goals, treatment is required for those who are already obese for their weight as well as lipid profile management. Surprisingly, however, treatment options remain quite limited. Lifestyle changes in the form of dieting and/or exercise per se do not generally produce marked or sustainable management of weight and lipid profile. This is how the use of medicines comes into picture in the form of synthetic drugs for weight management and as well as lipid profile management. Currently available options for lipid management are statins, which reduce low-density lipoprotein cholesterol, total cholesterol, and triglycerides and slightly increase high-density lipoprotein cholesterol. However long term administration of these drugs result in renal toxicity, hepatotoxicity as well as myalgia, thus resulting in hampered patient compliance due to these side effects. Further treatments for weight management are amphetamine derivatives, orlistat, sibutramine, rimonabant and other combination agents, which exhibit side effects related to cardiovascular risk, pulmonary hypertension and abuse potential, thus limiting their use for long term. Hence there is a need for alternate better options, such as agents of natural origin for managing healthy lipid profile as well as taking care of appetite and maintaining body weight. *Salacia* is a large woody climber grown in the rain forests of Western India and Sri Lanka. *Salacia reticulata* and *Salacia oblonga* are two major species of the plant that are known for health benefits, although other species such as *Salacia fimbrisepala, Salacia mamba, Salacia miegei, Salacia petenensis, Salacia chinensis* exist. Till date *Salacia* is evaluated and known for its use for treating various conditions such as diabetes, metabolic disorders, constipation, skin ailments, bacterial infections, bile acid regulation and as a nutritional supplement. In general, *Salacia* extracts are obtained by employing aqueous, organic or combination solvent systems from the roots and aerial parts and are specifically useful in the management of diabetes. Several patents and research publications relate to this extraction and evaluation of health applications of *Salacia*. Patents and patent applications such as U.S. Pat. Nos. 8,241,677, 8,337,911, EP2054070, EP 2397039, US20120100248, US20020004190, WO2008136013 describe use of *Salacia* extract for treatment of diabetes by mechanism of alpha-glucosidase enzyme inhibition.

Patent literature WO 200172316, WO 2008142702, WO 2012024270, U.S. Pat. No. 7,553,502, US20140186466, US20110236488, US20090263505, US20080102144 relate to use of *Salacia* extract in combination with other plant extracts for treatment of diabetes and other metabolic disorders as a result of synergistic effect.

Several non-patent literature references also describe use of *Salacia* for treating several health ailments. Mangiferin, one of the main components in *Salacia* species (Li et al. (*Life Sciences* 75:1735-1746, 2004), has been reported to be potent α-glucosidase inhibitors that have been shown to inhibit increases in serum glucose levels (Yoshikawa et al. *Yakugaku Zasshi* 123: 871-880, 2003). Aqueous extract of *S. reticulata* stems administered to normal mice resulted in reduced obesity, thus potentially could reduce the risk of associated diseases including type II diabetes (Im et al. 2008). However, these references do not teach effect of *Salacia* non-aqueous extract on food intake or appetite in the management of obesity.

Orally administered aqueous extract of *S. reticulata* prepared from the root bark to streptozotocin-induced diabetic rats exhibited blood glucose lowering effects of *S. reticulata* (Serasinghe et al. *Phytotherapy Research* 4: 205-2061990). The traditional anti-diabetic property of this natural medicine is attributable to intestinal α-glucosidase inhibitory activity (Yoshikawa et al. *Bioorganic & Medicinal Chem* 10: 1547-1554, 2002). Yoshikawa et al. *J Nutr.* 132:1819-1824, 2002), observed that an aqueous extract of *S. reticulata* roots could suppress body weight gain in female Zucker rats. All these references relate to aqueous extract of *Salacia* and none of these references relate to effect of such extract on appetite or on inhibition of HMG-CoA Reductase.

U.S. Pat. No. 8,114,445 relates to a dietary supplement containing an extract product of *Salacia*, an extract product of *Lagerstroemea speciosa*, an extract product of French maritime pine bark, an extract product of *Pterocarpus marsupium*, and an extract product of *Syzygium cumini*, said composition being administered in an amount effective to promote wellness and weight loss in the subject.

U.S. Pat. No. 8,420,131 relates to a pharmaceutical composition for treating obesity in a patient consisting essentially of effective amounts of: (1) *Rhodiola rosea* extract, (2) banaba leaf extract, and (3) an extract selected from the group consisting of: *Gardenia fructus* extract, apple extract, *Salacia reticulata* extract and mixtures thereof. The reference discloses synergistic effect of composition having various plants along with *Salacia*.

US20100247501 relates to a foodstuff comprising an extract of a plant of genus *Salacia* and a flavonoid which carries out suppression of obesity, after meal blood sugar level increase and fat. US Patent application 20120276081 provides a body weight gain suppressing composition including a composition of α-glucosidase activity inhibitor and a lipid synthesis inhibitor components. The α-glucosidase activity inhibitor is derived from at least one plant selected from *Salacia* genus plants, touchi and mulberry, and the lipid synthesis inhibitor component is selected from soybean peptide, marine animal peptide, and sesame lignin. These patent references focus on use of *Salacia* as an inhibitor of α-glucosidase which is combined with other plant components such as flavonoid and soybean which control body weight gain by inhibiting alpha glucosidase and lipid synthetase. However there are no studies on the effect of *Salacia* alone on appetite or HMG-CoA Reductase inhibition.

US20080241292 relates to a nutritional composition for promoting weight loss by jointly and simultaneously suppressing appetite, increasing satiation, decreasing the metabolic breakdown of carbohydrates and decreasing the absorption of carbohydrates in an individual comprising, effective amounts of an extract of Mulberry leaf, pinolenic acid and an extract of *Salacia oblonga* is provided.

US20080220098 relates to the combination of α-amylase inhibitors prepared from *Phaseolus vulgaris* with α-glucosidase inhibitors obtained from *Salacia oblonga* and other species. The α-amylase inhibitor is accompanied by a quantity of lectins that reduces the amount of glucose originating from the starches present in the diet, and considerably reduces the appetite after repeated administration. The combination with α-glucosidase inhibitors, such as extracts of *Salacia* or the thiosugars present in it, further reduce the blood glucose, acting synergistically, and consequently reduce the synthesis of fats from carbohydrates.

US20070037870 relates to aqueous extract prepared from *Salacia* which contain reticulanol and is effective in controlling blood sugar levels and as a result of this preventing obesity in diabetic patients.

WO2013016742 relates to a composition for treating obesity which includes a mood enhancer, an insulin sparing agent, and a peripheral energy blocker, wherein the mood enhancer contains inositol, *rhodiola rosea*, magnesium and zinc; the insulin sparing agent includes berberine, banaba leaf and inositol and the peripheral energy blocker contains a combination of a lipase and a glucosidase inhibitor such as *salacia*. The combination is evaluated for BMI reduction and weight loss for obesity claim.

SUMMARY

Compositions of *Salacia* have been made from aqueous, hydroalcoholic and methanolic extraction of roots and aerial parts and its health benefits mainly in terms of reducing blood sugar in diabetic subjects. Commercially, numerous products are available for the effective management of diabetes through reduced blood sugar. The mechanism for the blood sugar lowering property has been elucidated and the specific components of *Salacia* extracts have been found to reduce sugar intake by inhibiting enzyme alpha glucosidase. Synergistic effect of *Salacia* has also been combined with other natural products for various applications including obesity treatment. Some of these extracts are made with solvents such as ether, chloroform, methanol which are not of food grade and not useful as dietary supplement. However none of the references above relate to the effects of *Salacia* on enzymes involved in fat synthesis or break-down, such as HMG-CoA Reductase or to the effects on appetite, which may significantly reduce body weight and prevent weight gain.

As to the *Salacia* compositions described herein, Applicant has carried out extensive experimentation and surprisingly found out that extract of *Salacia* prepared by employing non-aqueous solvents results in new compositions comprised of combination of polyphenols, mangiferin, and 25,26-oxidofriedelane-1,3-dione in certain percentage by weight. Such compositions significantly reduce appetite, activate Hormone Sensitive Lipase and inhibit HMG-CoA Reductase enzyme, thus managing a healthy lipid profile. These effects are very important for an obese person, who is prone to ailments such as dyslipidemia and deposit of triglycerides in blood vessels, leading to coronary diseases. *Salacia* compositions described herein are safe for consumption and significantly slowed body weight gain, reduced food intake, decreased fat pad mass and increased fecal fat excretion, thus contributing to overall weight management. *Salacia* compositions described herein are prepared by an economic way and the solvents employed for extraction are safe for nutraceutical applications. Such compositions are useful for prevention and treatment of coronary heart disorders and associated cardiovascular complications. In one embodiment, a *Salacia* composition is described which significantly reduces appetite, activates Hormone Sensitive Lipase and manages healthy lipid profile by inhibiting HMG-CoA Reductase enzyme.

In one embodiment, a *Salacia* composition, essentially in the form of an extract, is comprised of polyphenols, mangiferin and 25,26-oxidofriedelane-1,3-dione in certain percentage by weight of the extract composition.

In one embodiment, a composition is comprised of a minimum of 12% polyphenol, of 2% mangiferin, and of 1% 25,26-oxidofriedelane-1,3-dione by weight of the extract. In some embodiments, a composition comprises at or about 12% polyphenol, 2% mangiferin, and 1% of 25,26-oxidofriedelane-1,3-dione by weight of the extract.

In one embodiment, a *Salacia* extract composition is prepared by a specific extraction technique employing non-aqueous solvents which are food grade.

In one embodiment, a method of treatment is described which includes administering *Salacia* composition to an individual in need thereof, in an effective amount. The individual in need thereof may be obese or overweight person who is suffering from dyslipidemia and risk of coronary heart diseases.

In one embodiment, a composition is described that helps maintain a healthy lipid profile, specifically by way of inhibition of HMG-CoA Reductase, an enzyme involved in the biosynthesis of cholesterol.

In one embodiment, a *Salacia* composition is described which exhibits significant lipolytic activity through activation of Hormone Sensitive Lipase. More particularly, in some embodiments, a *Salacia* composition is provided, which causes substantial weight reduction through lipolysis, by phosphorylation of Hormone Sensitive Lipase.

In one embodiment, a *Salacia* composition is provided which significantly slowed body weight gain, decreased fat pad mass and increased fecal fat excretion, thus contributing to overall weight management.

In one embodiment, a composition of *Salacia* is provided that significantly reduces the appetite and therefore energy intake leading to prevention of body weight gain following normal or high fat meal.

In one embodiment, a *Salacia* composition is provided for weight control and managing healthy lipid profile, which is produced economically, and is safe as a dietary supplement, and by reducing risk of coronary heart diseases and related cardiovascular complications.

*Salacia* compositions, methods of their preparation, and methods of treatment by their use significantly reduces appetite, activates Hormone Sensitive Lipase and manages healthy lipid profile by inhibition of HMG-CoA Reductase enzyme. The composition is in the form of extract which is prepared by cost efficient extraction technique employing solvent system which is food grade. The composition is comprised of at least about 12% polyphenols, 2% mangiferin and 1% of 25,26-oxidofriedelane-1,3-dione by weight of the composition. *Salacia* compositions herein and by their administration exhibit for example effects of significantly reduced appetite, when administered in an effective amount. The compositions enhance lipolysis through the activation of Hormone Sensitive Lipase and manage healthy lipid profile through inhibition of HMG-CoA Reductase enzyme. The synergistic effect of reduced appetite and regulation of enzymes involved in lipid metabolism, make it useful for managing healthy a lipid profile and simultaneous weight management such as in an obese individual. *Salacia* compositions described herein are safe for consumption and significantly slowed body weight gain, reduced food intake, decreased fat pad mass and increased fecal fat excretion, thus contributing to lowered coronary heart disorders and related cardiovascular complications.

BRIEF DESCRIPTION OF THE DRAWINGS

FIG. 1 shows high performance thin layer chromatography (HPTLC) fingerprint images of a *Salacia* composition from Example 1.

FIG. 2 is a graph showing the effect of *Salacia* composition on pancreatic lipase.

FIG. 3 is a graph showing the effect of *Salacia* composition on alpha-glucosidase enzyme.

DETAILED DESCRIPTION

*Salacia* compositions, methods of their preparation, and methods of treatment by their administration are described herein, which for example significantly reduce appetite, activate Hormone Sensitive Lipase and manage a healthy lipid profile such as by inhibition of HMG-CoA Reductase enzyme.

As used herein, the term "*Salacia* composition" refers to the product obtained by extraction from genus *Salacia*, using its aerial, sub aerial or underground plant parts. The extract is prepared by employing food grade non aqueous solvents, which are safe for human consumption. The composition is comprised of polyphenols, mangiferin, and 25,26-oxidofriedelane-1,3-dione in certain percentages by weight of the composition. In some embodiments, the composition is in the form of an extract, where the amounts of polyphenols, mangiferin, and 25,26-oxidofriedelane-1,3-dione in are present in certain percentages by weight of the extract.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The term "reduced appetite" refers to the effect observed in an individual when an effective amount of the *Salacia* composition is administered over a period of time and results in reduced food intake as compared to a regular diet. This effect is beneficial in individuals who tend to be obese due to overeating. Reduced appetite helps to reduce energy intake.

Further the term "healthy lipid profile" refers to blood lipid levels of an individual, which relates to amounts of low density lipoproteins (LDL), high density lipoproteins (HDL), total cholesterol and triglycerides. LDL is known as bad cholesterol and HDL is good cholesterol. LDL gets deposited in coronary arteries and thus leads to artheroscle-rosis and related coronary heart disease. HDL avoids deposition of fats in the blood vessels, and hence higher amounts of HDL are desired for healthy lipid profile. The individuals, who tend to eat more, suffer from energy imbalance and tend to be obese, also develop dyslipidemia, in the form of increased levels of LDL and triglycerides. This condition needs to be treated for reducing food intake as well as managing healthy lipid profile.

When a *Salacia* composition as described herein is administered to an individual in need thereof in an effective amount, the effects are observed in the form of significantly reduced food intake, activation of Hormone Sensitive Lipase, and inhibition of HMG-CoA reductase enzyme. The composition is also found to inhibit pancreatic lipase and alpha glucosidase enzyme.

As used herein, the terminology "effective amount" means the amount of *Salacia* composition which when administered over a specific time period to individuals in need thereof, results in the desired beneficial outcome. The subject/individual in need thereof, in this context is one who is suffering from dyslipidemia being overweight or who has a high body mass index (BMI) and has the tendency to be obese. Such individuals with a disturbed lipid profile and higher weight are at high risk of myocardial infarction, ischemic heart diseases and cardiac arrest.

I. Preparation of *Salacia* Composition

According to one embodiment, a *Salacia* composition is prepared by non-aqueous solvent extraction method by using dried plant parts of Genus *Salacia*.

According to one embodiment, a process for preparation of novel *Salacia* composition is comprised of drying and grinding aerial, sub-aerial or underground plant parts of *Salacia*, stirring *Salacia* plant parts with food grade non-aqueous polar solvent at ambient to an elevated temperature and filtering the non-aqueous solvent. *Salacia* plant material remaining after filtration is stirred again with food grade non-aqueous solvent to an elevated temperature and the non-aqueous solvent is again filtered from system. Filtrates are combined and evaporated to obtain *Salacia* composition in the form of an extract. As per another embodiment, different species of *Salacia* include examples such as *Sala-*

*cia reticulata, Salacia oblonga, Salacia fimbrisepala, Salacia mamba, Salacia miegei, Salacia petenensis, Salacia chinensis*, and the like.

In one embodiment, *Salacia reticulata* and/or *Salacia oblonga* are preferred plant varieties for extraction. In some embodiments, dried roots of *Salacia reticulata* are selected for obtaining a *Salacia* composition.

In some embodiments, dried and coarsely ground plant parts of *Salacia reticulata* are extracted with food grade non-aqueous polar solvents to obtain a composition, which is safe for human consumption.

In some embodiments, roots of *Salacia reticulata* are extracted with non-aqueous food grade solvent such as ethanol, isopropyl alcohol, n-butanol, acetone, or the mixtures thereof. In another embodiment, the solvent is preferably ethanol and it is employed in a weight to volume ratio of *Salacia* and solvent such as at or about 1:2 to at or about 1:30. As one example, the weight to volume ratio may be in some circumstances 100 gm *Salacia* parts (e.g. roots) and 200 ml solvent (e.g. ethanol) when the weight to volume ratio is 1:2.

Dried roots of *Salacia* for example in powdered form are mixed with solvent and stirred at ambient to an elevated temperature range of 85° C. for 2 to 16 hours. The solvent is then filtered under vacuum using for example a Buchner funnel.

In some embodiments, remaining *Salacia* roots can be re-extracted with appropriate volumes of ethanol by stirring at ambient to an elevated temperature. Filtrates obtained through such extraction processes are combined and processed to get a dry powder of *Salacia* extract, resulting in a *Salacia* composition.

II. Characterization of *Salacia* Composition

In one embodiment, a *Salacia* composition in the form of an extract is subjected to characterization to identify the components which form the extract composition. Fractionation of *Salacia* composition is carried out using suitable solvent systems. In one embodiment, a system of polar and non-polar solvents can be employed to separate fractions of *Salacia* composition. The solvents employed in a process for fractionation of *Salacia* extract may be selected from the group such as, but not limited to, acetone, hexane, ethyl acetate, isopropyl alcohol, ethanol, dichloromethane, methanol, water and a mixture thereof, more preferably from acetone, ethanol, dichloromethane, isopropyl alcohol, and more preferably dichloromethane and isopropyl alcohol. In a preferred embodiment the non-polar solvents which may be used for fractionation of *Salacia* extract include, but not limited to, petroleum ether (low boiling), petroleum ether (high boiling), hexane and the like or the mixtures thereof. In another preferred embodiment, the polar solvents, which may be used for this process, include, but is not limited to, isopropyl alcohol, acetone, methanol, ethanol, acetonitrile or mixtures thereof.

The fractions obtained by treatment of appropriate solvents can be combined and purified by appropriate techniques to get enriched components. These components can be identified by different analytical techniques such as column chromatography, thin layer chromatography (TLC) or High performance thin layer chromatography (HPTLC) using silica gel. This identification leads to understanding of the *Salacia* chemical composition.

III. In-Vitro Testing of *Salacia* Composition

Compositions herein may be used in accordance with the methods of the present disclosure, which comprise the oral administration of effective amounts of the composition to individuals in need of weight control and lipid management.

These beneficial effects may be achieved by activation and inhibition of certain enzymes involved in body metabolism. The composition helps to significantly reduce appetite, activates Hormone Sensitive Lipase and inhibits HMG-CoA Reductase enzyme, thus managing healthy lipid profile.

The methods are especially useful in individuals afflicted with hyperlipidemia, individuals afflicted with type 2 diabetes, overweight or obese individuals, individuals with impaired glucose tolerance, individuals at risk for coronary heart diseases or other individuals who may otherwise benefit from weight and blood lipid control. All these benefits are made possible by the methods and compositions described herein.

In accordance with the methods described herein, the effect of *Salacia* composition is studied in vitro on enzymes involved in the metabolism of fats. The study is carried out through enzyme assay. The enzymes considered for this testing may be HMG-CoA Reductase, Hormone Sensitive Lipase, pancreatic lipase and the like.

In one embodiment, a *Salacia* composition may be tested to assess its activity on HMG-CoA (3-Hydroxy-3-Methyl-Glutaryl-Coenzyme-A) reductase enzyme. This is a rate controlling enzyme of the mevalonate pathway, a metabolic pathway that produces cholesterol and other isoprenoids in the body. By inhibiting this enzyme it is possible to prevent production of excessive cholesterol and thus help maintain a healthy lipid profile.

Hormone Sensitive Lipase is an enzyme involved in the break-down of fat in the adipose tissue. Activation, in the form of phosphorylation of this enzyme can result in increased breakdown of fats, in other terms, causes significant lipolysis.

*Salacia* compositions herein may be assessed for activity on both these enzymes and it is found to increase the activation of Hormone Sensitive Lipase and inhibit HMG-CoA reductase in a significant manner. The composition can also be assessed for its ability to breakdown triglycerides to glycerol and free fatty acids by mechanism of lipolysis. The composition maintains healthy lipid profile by inhibiting enzyme HMG-CoA Reductase at IC50 of not less than 400 µg/ml. Such compositions therefore, can be employed for its weight and lipid management effect.

*Salacia* compositions herein may be also tested for its activity on Pancreatic lipase enzyme to assess ability to prevent fat absorption and compared against positive control to check for its effect.

Activity of *Salacia* compositions herein may be assessed on alpha glucosidase enzyme for its effect on prevention of carbohydrates absorption and compared with positive control. The activity can be determined by using appropriate assay technique to check inhibitory effect in terms of IC50.

*Salacia* compositions may also be evaluated in vitro for their antioxidant and anti-inflammatory activity as these activities are beneficial for individuals, who are at risk because of dyslipidemia and artherosclerosis due to deposition of fat in blood vessels. Antioxidant activity may be assessed for capacity of *Salacia* composition to directly react with and quench free radicals. A free radical is any chemical species (capable of independent existence) possessing one or more unpaired electrons. Free radicals are formed from molecules via the breakage of a chemical bond such that each fragment keeps one electron by cleavage of a radical to give another radical and, finally via redox reactions. Oxidative stress is the term referring to the imbalance between generation of reactive oxygen species and the activity of the antioxidant defenses. The implication of oxidative stress in the etiology of several chronic and acute degenerative disorders suggests that antioxidant therapy represents a promising avenue for treatment. The role of antioxidant therapy is very significant in the intervention and prevention of cardiovascular diseases, where treatment with synthetic antioxidants, dietary antioxidant factors from food plants and medicinal plants may potentially prevent or reverse the promotion or progression of such diseases.

IV. In-Vivo Evaluation of *Salacia* Composition

*Salacia* compositions described herein may be evaluated in-vivo for their effect on controlling appetite and managing a healthy lipid profile. In some embodiments, a composition herein is comprised of an extract, such as an ethanolic extract, and which can exhibit action on the enzymes responsible for body metabolism. It will be appreciated that other solvents, such as for example but not limited to any food grade solvent, e.g. food grade polar solvents, may be employed in obtaining the extract, and which may or may not include ethanol. In vitro experiments demonstrate that HMG-CoA enzyme is inhibited by a *Salacia* composition as described herein, thus its effect is evident on managing a desirable blood lipid profile. These beneficial effects are further supported by antioxidant and anti-inflammatory activities exhibited by *Salacia* compositions herein and thus support their application for cardiac ailments in obese individuals.

*Salacia* compositions herein are evaluated for their effect on inducing weight loss or preventing weight gain, food intake (satiety), food efficiency and fecal fat excretion. Studies were conducted on obese mouse by feeding an effective amount of *Salacia* composition over a period of 7.5 weeks and the effects observed in comparison to untreated obese mouse as the positive control. The outcomes are recorded for high and low dose of *Salacia* composition. The observations from these evaluations indicate significantly lowered body weight gain, reduced food intake and increased fecal fat excretion, thus contributing to reduced fat absorption. Effect of *Salacia* compositions herein on reduced satiety is beneficial for individuals who suffer from obesity due to overeating, thus accumulating extra fats, evident in the form of increased body weight as well as dyslipidmia. This excessive fat and cholesterol gets deposited in the blood vessels supplying blood to vital organs and lead to inflammation and atherosclerotic problems, putting excessive burden on cardiovascular system. The in vivo evaluation observations are also in concordance with in vitro effects.

*Salacia* compositions herein are effective for reducing appetite and managing healthy lipid profile and are safe for consumption. The composition reduces food intake for about 12 to 18%, when administered in effective amounts to an individual in need thereof over a period of 7.5 weeks. The composition does not show adverse effects on body cells and organs as observed during the in-vivo evaluation. The compositions herein are evaluated for in-vitro effects on enzymes involved in metabolism and the outcomes are further confirmed in the form of in-vivo evaluation for effect on body weight, food intake, food efficiency and fecal fat excretion. In one embodiment, compositions herein are prepared by an extraction method from *Salacia* plant parts, employing non-aqueous food grade solvent. In some embodiments, the composition is in the form of dry powder and comprises polar and mid-polar components, which are characterized by chemical as well as chromatographic methods.

The compositions can be administered to individuals in need thereof, in the form of powder, or reconstituted with suitable vehicle, prior to administration or can be formulated in suitable solid or liquid dosage form, convenient for oral or parenteral administration. According to the invention, this composition is evaluated through in-vitro, in-vivo experiments to determine benefits for weight and lipid management. The outcomes are desirable in terms of HMG-CoA inhibition as well as lipolysis activation through hormone sensitive lipase activation, reflecting into reduced bogy weight, reduced food intake and increased fecal fat excretion during animal study.

While specific illustrative embodiments have been described, certain modifications and equivalents will be apparent to those skilled in the art and are intended to be included within the scope of the invention as set forth in the claims below. The details and advantages the compositions and methods described herein are explained hereunder in greater detail in relation to non-limiting exemplary illustrations.

EXAMPLES

Example 1: Preparation of *Salacia* Composition

*Salacia reticulata* roots are dried, ground and extracted with 5 volumes of ethanol by stirring at 60-65° C. for 3 hrs. The solvent is then filtered under vacuum and the filtrate is set aside. The material is re-extracted with 3 volumes of ethanol by stirring at 60-65° C. for 1 hr. The solvent is filtered and the filtrates are combined and then evaporated on a rotary evaporator at 50° C. to obtain dry reddish brown powder of extract.

The results herein are based on the resulting composition of Example 1, representing one embodiment of a *Salacia* composition herein. The composition of Example 1 is comprised of at least 12% polyphenols, at least 2% mangiferin, and at least 1% 25,26-oxidofriedelane-1,3-dione by weight of the composition.

Compositions based on Example 1 in some embodiments contain at or about 16% total polyphenols, at or about 3% mangiferin, and at or about 2.6% of 25,26-oxidofriedelane-1,3-dione, by weight of the composition, for example when calculated as an average of multiple batches prepared by following the same process.

It will be appreciated that in some embodiments, compositions herein can include as high as amounts of about or up to 39% total polyphenols, about or up to 7.36% mangiferin, and about or up to 3.17% 25,26-oxidofriedelane-1,3-dione by weight of the composition.

Example 2 A: Isolation and Characterization of *Salacia* Composition Determination of Total Polyphenols Content (as Gallic Acid Equivalent) by UV

*Salacia* composition is dispersed in methanol in desired concentration and 1.0 ml of each sample is taken into test tube and mixed with 5 ml of a 10 fold dilute Folin-Ciocalteu reagent and 4 ml of 7.5% sodium carbonate. The tubes are covered with parafilm and allowed to stand for 50 minutes at room temperature. Then the absorbance was read at 765 nm spectrometrically against Gallic acid as a standard.

Determination of Mangiferin and its Derivatives:

The estimation of mangiferin and its derivatives from *Salacia* composition is done by HPLC. The column used is Merck LiChrospher 100 RP 18, 250×4 mm, 5 µm. The flow rate is 1.0 mL per minute and the detector wavelength is 260 nm. A gradient run is with 0.05% orthophosphoric acid (OPA) as mobile phase A and MeOH:ACN (Methanol: Acetonitrile) (3:2) as mobile phase B. For sample preparation approx. 25-30 mg of the extract is dissolved in 25 ml of methanol. The solution is filtered using 0.45µ filter paper. Retention time of Mangiferin is 20 mins.

Isolation & Characterization of 25,26-oxidofriedelane-1,3-dione

Salacia composition of Example 1 is further dissolved in acetone and the soluble part is subjected to a TLC (Thin Layer Chromatography) pattern and is chromatographed over silica gel (100-200 mesh) using hexane:ethyl acetate (95:5, 90:10, 85:15, 80:20, 75:25, 70:30) as eluents. The fractions are combined and concentrated and further purified using hexane:dichloromethane mixtures and recrystallized using hexane to obtain 25,26-oxidofriedelane-1,3-dione in pure form. The content of 25,26-oxidofriedelane-1,3-dione is determined by high performance liquid chromatography (HPLC) and it is further characterized by high performance thin layer chromatography (HPTLC) fingerprinting.

Method for Estimation of 25,26-oxidofriedelane-1,3-dione:

The estimation of 25,26-oxidofriedelane-1,3-dione from Salacia composition is done by HPLC. The column used is Merck LiChrospher 100 RP 18, 250×4 mm, 5 µm. The flow rate is 1.0 mL per minute and the detector wavelength is 260 nm. A gradient is run with 0.1% Formic Acid:Methanol:water (80:20) as mobile phase A and 0.1% Formic Acid in Methanol as mobile phase B. For a sample preparation, approx. 25-30 mg of the extract is dissolved in 25 ml of methanol. The solution is filtered using 0.45µ filter paper. Retention time of 25,26-oxidofriedelane-1,3-dione is 30 minutes.

HPTLC Profile of Salacia Composition with 25,26-oxidofriedelane-1,3-dione and Mangiferin HPTLC profile of Salacia composition of the invention is checked and compared with 25,26-oxidofriedelane-1,3-dione fraction using non-polar solvent system (mobile phase—Hexane:Ethyl acetate) and with mangiferin using polar solvent system (Ethyl Acetate:Acetone:Formic acid:Water [6:2:0.5:0.5]) and the bands are detected at wavelength of 254 nm (see FIG. 1).

Example 3: In-Vitro Evaluation of Salacia Composition Through Enzyme Assays

Salacia composition is assessed in vitro for its effect on HMG-CoA Reductase enzyme to assess application for maintaining healthy lipid profile. The effect is further also assessed on enzymes such as Hormone Sensitive Lipase and pancreatic lipase.

a. HMG-CoA Reductase Assay

Methodology:

HMG-CoA Reductase enzyme is the rate-limiting step in cholesterol synthesis. The activity of HMG-CoA Reductase is assessed using HMG-CoA reductase assay kit (Sigma CS 1090). It measures the oxidation of NADPH (Nicotinamide adenine dinucleotide phosphate) by the catalytic subunit of HMG Reductase in the presence of the substrate:HMG-CoA at the absorbance 340 nm.

Results:

The Salacia composition, such as that of Example 1 inhibits HMG-C0A at a concentration of 1 mg/ml with IC50: 401.3 µg/ml (Table 1).

TABLE 1

Effect of Salacia composition on HMG-CoA Reductase enzyme

| Salacia composition concentration (mg/ml) | % inhibition |
|---|---|
| 0.01 | 0 |
| 0.1 | 4.16 |
| 1 | 100 | b. Pancreatic Lipase Assay

Methodology:

The objective of this assay is to assess ability of Salacia composition to prevent fat absorption. Pancreatic lipase activity is assessed using pancreatic porcine lipase and 4-methylumbelliferyl oleate (MU Oleate) as substrate. Orlistat is used as a positive control. Lipase activity is measured using a fluorescence kinetic assay.

Results:

Salacia composition displayed a significant inhibitory effect against pancreatic lipase, compared to orlistat (Table 2).

TABLE 2

Effect of Salacia composition on pancreatic lipase enzyme

| Extract | IC50 (µg/ml) |
|---|---|
| Salacia composition | 10.12 |
| Orlistat | 0.53 |

Pancreatic lipase is a key enzyme that hydrolyzes triacylglycerols to monoacylglycerols. In vitro studies showed that the Salacia composition, such as that of Example 1, possesses a strong pancreatic lipase inhibitory activity. See FIG. 2. IC50 value of Salacia composition is comparable to orlistat, a clinically approved drug as lipase inhibitor. Salacia compositions herein reduce energy intake by inhibiting dietary fat absorption via pancreatic lipase inhibition.

c. Lipolysis Assay

Methodology:

The assay is carried out to assess the ability of the extracts to breakdown triglycerides to glycerol and free fatty acids. The Salacia composition, such as that of Example 1 was screened for lipolysis in 3T3L1 cell model. 3T3L1 preadipocytes were cultured for a week in Dulbecco modified Eagle's medium (DMEM) supplemented with 10% new calf serum, 25 mM glucose, 2 mM glutamine, 100 U/ml penicillin, 100 ug/ml streptomycin at 37° C. in 5% CO2 atmosphere until 100% confluence.

Two days after confluence, the differentiation of 3T3L1 into adipocytes was initiated using (DMEM) supplemented with 10% fetal bovine serum (FBS), 25 mM glucose, 2 mM glutamine, 100 U/ml penicillin, 100 ug/ml streptomycin and differentiation inducers (0.5 mM isobutyl-methylxanthine (IBMX), 10 µg/ml insulin and 1 µM dexamethasone) for 48 h (day 0-day 2). The cells were then cultured for another 48 h with the same medium containing only 10 µg/ml insulin (day 2 to day 4), then with only the medium (day 4 to day 6). The Salacia composition, such as that of Example 1 was added to the medium at the concentration 100 ug/ml for 24 h and assessed for lipolysis. The effect of the Salacia composition, such as that of Example 1 was compared to a positive control isoproterenol (10 uM).

The glycerol released after 24 h in the cell media was assessed using glycerol reagent (sigma) and expressed relative to the cellular protein content. The protein content was assessed using bicinchoninic acid (BCA) Pierce™ kit. If the extract displays a ratio of glycerol/protein higher than 1.40, it is considered as an extract that enhances lipolysis. Proteins were collected from cell lysates of 3T3L1 adipocytes treated for 24 h with the Salacia composition or isoproterenol. Protein samples were blotted and probed for total hormone sensitive lipase (HSL), and phosphorylated hormone sensitive lipase at Serine 563. Then, the ratio of phosphorylated-HSL to total HSL was compared between treated and non-treated samples.

Results:

The *Salacia* composition, such as that of Example 1 displayed a ratio higher than 1.40, suggesting that it enhances lipolysis in 3T3L1 cells (Table 3).

TABLE 3

Effect of Salacia composition on Lipolysis

| Extract | Glycerol/protein ratio |
|---|---|
| Salacia composition | 1.83 |
| Isoproterenol | 1.50 |

In-vitro studies also showed that *Salacia* composition treatment induced a strong lipolysis in 3T3L1 cells. This lipolytic effect on adipocytes cells was equivalent to the effect of isoproterenol, a beta-adrenergic receptor agonist, known for his lipolytic activity.

d. Hormone Sensitive Lipase Assay

The *Salacia* composition, such as that of Example 1 induced a significant increase in the phosphorylation of hormone sensitive-lipase, almost at the same extent than the positive control, isoproterenol, confirming the lipolytic effect of the *Salacia* composition shown by the increase of glycerol (Table 4).

TABLE 4

Western blot densitometric analysis of Hormone Sensitive lipase (HSL) and Phosphorylated HSL (Phospho-HSL) isolated from adipocytes lysates

| Samples | Phospho-HSL | Total HSL | Ratio phosphorylated-HSL/Total HSL |
|---|---|---|---|
| Non-treated | 1.00 | 1.00 | 1.00 |
| Salacia composition | 2.43 | 2.14 | 1.14 |
| Isoproterenol | 2.63 | 2.60 | 1.01 |

*Salacia* composition treatment enhanced phosphorylation of the hormone-sensitive lipase which hydrolyzes the triglycerides into nonesterified fatty acids and glycerol. The increased glycerol levels in adipocytes treated with the *Salacia* compositions, such as that of Example 1 were almost at the same extent that the positive control:isoproterenol, confirming that acute treatment with *Salacia* composition enhances lipolysis. Lipolytic effect of the *Salacia* composition was thus correlated with a significant increase (a factor of 2.43) in hormone sensitive lipase phosphorylation.

e. Alpha Glucosidase Assay

Methodology:

The objective of this assay is to assess the prevention of carbohydrates absorption. Alpha-glucosidase is an enzyme that breaks downs the carbohydrates into absorbable monosacharides. The activity of α-glucosidase is assessed using mammalian α-glucosidase extracted from rat intestinal acetone powder (Sigma) and p-nitrophenyl L-D glucopyranoside (PNPG) as an artificial substrate. Acarbose is used as a positive control. Alpha-glucosidase activity is determined using a colorimetric kinetic assay by monitoring the release of PNPG at the absorbance 400 nm using a microplate reader Synergy H1.

Results:

The *Salacia* compositions, such as that of Example 1 showed a significant inhibitory effect on α-glucosidase. IC50 for the *Salacia* composition was 3.47 µg/ml compared to acarbose (IC50:19 µg/ml). (See FIG. 3)

In-vitro studies showed clearly that the *Salacia* composition such as that of Example 1 has a strong inhibitory effect on alpha-glucosidase activity and it is comparable to an established marketed alpha-glucosidase inhibitor acarbose Inhibition of alpha glucosidase delays glucose absorption into the blood and suppresses postprandrial hyperglycemia. These finding suggests that *Salacia* composition may have an anti-obesity effect via inhibition of carbohydrates absorption.

Example 4: In Vitro Evaluation of *Salacia* Composition Using Cell Lines a. Determination of Antioxidant Activity by DPPH (2,2-diphenyl-1-picrylhydrazyl) Assay The capacity of plant extracts or fractions to directly react with and quench free radicals was evaluated as described earlier (Cheng et al 2006). A stock solution of DPPH (200 µM) was prepared in ethanol. The assay was performed in 96-well plates. The reaction mixture, containing 100 µL of DPPH and 100 µL of test sample, was incubated at 37° C. for 30 min. The absorbance was measured at 515 nm. Gallic acid was used as a positive control. Percent DPPH radical scavenging activity was calculated as follows. [Reference: Cheng Z, Morre J, Yub L (2006) J Agric Food Chem, 54: 7429-7436]

% radical scavenging activity=[1−(sample−blank)/(control−blank)]×100

Gallic acid showed 86% radical scavenging activity at 20 µM. The *Salacia* composition such as that of Example 1 exhibited 84.3% radical scavenging activity which is quite significant and comparable to positive control activity.

Determination of Anti-Inflammatory Activity:

Inhibition of NOS (nitric oxide synthase) activity was determined in RAW264.7 cells. It was found that the *Salacia* composition showed iNOS activity with $IC_{50}$>50.

Thus in-vitro assays indicate that the *Salacia* composition inhibits HMG-CoA reductase enzyme, thus suggesting its application for maintaining a healthy lipid profile in individuals in need thereof. The composition is also found to enhance lipolysis by activating hormone sensitive lipase enzyme and inhibiting absorption of fat by inhibiting pancreatic lipase enzyme. The *Salacia* composition also reduced absorption of carbohydrates by inhibiting alpha-glucosidase enzyme, thus contributing to decreased energy intake. The composition also demonstrates antioxidant and anti-inflammatory activity.

The *Salacia* composition, such as that of Example 1 was also subjected to in-vivo study to investigate its role in obese rat models.

Example 5: In-Vivo Study for *Salacia* Composition

Fifty-six (56) male C57BL/6 mice were purchased from Charles River, at the age of 5 weeks. The mice were housed individually in mouse cages in a temperature-controlled room with a 12-hour light and dark cycle and free access to regular rodent chow and water. After a week of adaptation, the mice were divided into 7 groups with 8 mice in each group. All mice were fed a high-fat diet (60% energy from fat) to induce obesity. Six groups were gavaged with low (100 mg/kg/d) and high (500 mg/kg/d) doses of *Salacia* composition suspending in 0.5% carboxymethyl cellulose, respectively for 7.5 weeks (52 days exactly).

One group was used as the obese control and gavaged with the vehicle control. Body weights were obtained daily and food intake was recorded thrice every week. Fecal samples were collected during weeks 6 and 7 by placing mice in metabolic cages for 3 days. At the end of the study, the mice were anaesthetized and blood samples were collected by cardiac puncture into serum tubes containing clot-activator and placed on ice until centrifugation for serum. Liver and epididymal fat pads were collected, rinsed with phosphate-buffered saline, and weighed. Liver, stomach, muscle, and adipose tissues were collected, frozen immediately in liquid nitrogen and stored, together with serum, at −80 C.

As the experiments were carried out for a period of 7.5 (52 days), the body weight and food intake were reported for up to 7 weeks. Other results, except for fecal fat excretion, were obtained at the end of the study (after 52 days of treatment).

a. Effect of *Salacia* Composition *Salacia* Composition on Food Intake (Appetite)

Data were analyzed using one-way ANOVA with repeated measures. Differences between treatments means were determined by pairwise comparisons using the least squares means test, where p<0.05 was considered significant. Results are presented as values with their standard errors (n=7-8).

c. Effect of *Salacia* Composition on Food Efficiency

FE (Food efficiency) was calculated as per gram of weight gain over 100 g of diet consumed. Data were analyzed using one-way ANOVA. Results are presented as values with their standard errors (n=7-8).

TABLE 5

Effect Salacia composition on food intake (appetite) in obese mice

| Treatment | Time post treatment (week) | | | | | | |
|---|---|---|---|---|---|---|---|
| | 1 | 2 | 3 | 4 | 5 | 6 | 7 |
| OBC[&] | 2.54 ± 0.08 | 2.49 ± 0.09 | 2.47 ± 0.09 | 2.50 ± 0.07 | 2.63 ± 0.06 | 2.36 ± 0.08 | 2.83 ± 0.07 |
| Salacia composition low dose | 2.63 ± 0.04 | 2.40 ± 0.09 | 2.42 ± 0.07 | 2.41 ± 0.06 | 2.47 ± 0.03 | 2.41 ± 0.08 | 2.56 ± 0.10 |
| Salacia composition high dose | 2.44 ± 0.09 | 2.35 ± 0.09 | 2.20 ± 0.12 | 2.20 ± 0.08* | 2.23 ± 0.13* | 2.21 ± 0.12 | 2.34 ± 0.14* |

[&]OBC, obese control
*different from the OBC, p < 0.05.

Data were analyzed using one-way (ANOVA), analysis of variance, with repeated measures. Differences between treatments means were determined by pairwise comparisons using the least squares means test, where p<0.05 was considered significant. Results are presented as values with their standard errors (n=7-8). In vivo study showed that *Salacia* composition treatment decreased food intake significantly, by about 20% in high fat diet mice. These results suggest that the *Salacia* composition, such as that of Example 1 may boost weight loss by reducing calories intake; its effect on energy intake is similar to sibutramine.

As indicated in Example 5, two different doses of *Salacia* composition were administered to experimental animals—100 mg/kg/day (low dose) and 500 mg/kg/day (high dose), wherein high dose *Salacia* composition resulted in statistically significant results, and which may be considered in some circumstances an effective amount. It will be appreciated that such results may also be observed in other doses or amounts between the high and low doses (or outside the high and low doses), and which may be effective to achieve the favorable results herein as may be desired or statistically significant results.

b. Effect of *Salacia* Composition on Body Weight

TABLE 7

Effect of Salacia composition on food efficiency

| Treatment | FE (g/100 g) |
|---|---|
| OBC | 10.8 ± 0.6 |
| Salacia composition low dose | 9.5 ± 0.5 |
| Salacia composition high dose | 6.4 ± 1.3[#] |

[#]different from OBC group, p = 0.0163 (p < 0.05)

Data were analyzed using one-way ANOVA. Differences between treatments means were determined by pairwise comparisons using the least squares means test, where p<0.05 was considered significant. Results are presented as values with their standard errors (n=7-8).

d. Analysis of Fecal Crude Lipids

Crude lipids were extracted from the feces collected over 48 hr, using a modified Folch method. Briefly, fecal samples were weighed into glass culture tubes and homogenized in presence of methanol. After 15 min in a shaking water bath, the tubes were cooled to the room temperature and hexane: chloroform mix (4:1, v/v) was added. After shaking for 10 min, 0.88% Sodium chloride solution was added. The tubes

TABLE 6

Effect of Salacia composition on the body weight in obese mice

| Treatment | Time post treatment (week) | | | | | | | |
|---|---|---|---|---|---|---|---|---|
| | 0 | 1 | 2 | 3 | 4 | 5 | 6 | 7 |
| OBC[&] | 19.9 ± 0.3 | 24.0 ± 0.2 | 26.1 ± 0.3 | 28.1 ± 0.4 | 29.7 ± 0.4 | 31.9 ± 0.5 | 33.3 ± 0.7 | 34.2 ± 0.8 |
| Salacia composition low dose | 19.8 ± 0.2 | 22.9 ± 0.2* | 25.4 ± 0.3 | 27.1 ± 0.5 | 29.0 ± 0.5 | 30.7 ± 0.6 | 32.1 ± 0.6 | 33.0 ± 0.7 |
| Salacia composition high dose | 19.8 ± 0.2 | 22.6 ± 0.2* | 24.6 ± 0.4* | 26.0 ± 0.5* | 27.0 ± 0.7* | 28.2 ± 0.9* | 29.2 ± 1.1* | 29.4 ± 1.3* |

*Salacia composition was different from OBC, p < 0.05.

were vortexed and centrifuged. The supernatant was collected into clean glass tubes. The extraction was repeated twice and the supernatants were pooled. The supernatant was then dried up and the total crude lipids were used to calculate fat excretion rate (% of the total fat consumed through the diet over the 48-hr fecal collection period).

TABLE 8

Effect of treatments on fecal fat excretion rate in male C57BL/J mice

| Treatment | % of fat excretion |
| --- | --- |
| OBC | 0.69 ± 0.08 |
| Salacia composition low dose | 0.66 ± 0.06 |
| Salacia composition high dose | 0.98 ± 0.10[#] |

[#]different from OBC group, p = 0.0163

Data were analyzed using one-way ANOVA. Differences between treatments means were determined by pairwise comparisons using the least squares means test, where $p<0.05$ was considered significant. Results are presented as values with their standard errors (n=7-8).

Results:

The *Salacia* composition, such as that of Example 1 significantly slowed body weight gain and reduced food intake in weeks 4, 5 and 7 over the 7.5-week treatment period, and increased fecal fat excretion. The average body weight of rats treated with the *Salacia* composition was 14% lower than the obese controls.

e. Histological Testing

At the end of the study, kidneys, liver, spleen, thymus, heart, lungs, stomach, small and large intestines, skeletal muscle and epididymal fat of mice in the obese control and having the *Salacia* composition (high dose) were harvested immediately after blood collection under anesthesia and fixed in 10% neutral buffered formalin for more than 48 hours. Appropriately trimmed (2-5 mm thickness) tissues were processed, embedded with paraffin, 4-5 micron sections were cut and stained with haematoxylin and eosin stain.

No treatment related changes were observed in this study. No abnormalities were detected during record of histopathological examination of Kidney, spleen, thymus, heart, stomach, small and large intestines, skeletal muscle and epididymal fat, when the *Salacia* composition, such as that of Example 1, was administered over a period of 7.5 weeks.

Results:

The *Salacia* composition of Example 1 significantly slowed body weight gain, reduced food intake, and increased fecal fat excretion at the dose of 500 mg/kg/d. These in-vivo findings are in concordance with in-vitro results where the *Salacia* composition has a strong inhibitory effect on pancreatic lipase activity, compared to orlistat (IC50 were respectively 10.12 μg/ml for the *Salacia* composition and 0.53 μg/ml for orlistat). Chronic treatment with high dose the *Salacia* composition showed a weight lowering effect, prevented body mass gain and decreased fat pad mass.

The *Salacia* composition can be employed at the dose of 500 mg/kg/day as a potential bioactive compound that slows body weight gain by reducing food intake and inhibiting HMG-CoA reductase enzyme, thus managing healthy lipid profile. Thus the *Salacia* composition is an emerging natural product that has multiple target enzyme regulatory activities which exhibit efficacy as an obesity treatment.

The invention claimed is:

1. A *Salacia* composition, comprising at least 12% polyphenols, at least 2% mangiferin, and at least 1% 25,26-oxidofriedelane-1,3-dione by weight of the composition, wherein a daily amount of the 25,26-oxidofriedelane-1,3-dione is at least 5 mg/kg, and the composition exhibits activity including reducing appetite, activating Hormone Sensitive Lipase, and/or maintaining a healthy lipid profile through inhibition of HMG-CoA Reductase enzyme, wherein the compounds are obtained from *Salacia* plant parts as an extract by a first extraction with a first solvent at 60° C.-65° C. for three hours, then filtration, and by a second extraction with a second solvent at 60° C.-65° C. for one hour, then filtration.

2. The composition of claim 1, wherein the extract consists essentially of at least 12% of polyphenols, at least 2% of mangiferin and at least 1% of 25,26-oxidofriedelane-1,3-dione by weight of the extract.

3. The composition of claim 1, wherein the extract is obtained by solvent extraction from aerial, sub-aerial, or underground parts of *Salacia* plant parts, or combinations thereof.

4. The composition of claim 1, wherein the extract is prepared from stems, leaves, or roots of *Salacia reticulata* and/or *Salacia oblonga*, or combinations thereof.

5. The composition of claim 1, wherein the extract is obtained using a food grade non-aqueous polar solvent.

6. The composition of claim 5, wherein the food grade polar non-aqueous polar solvent is selected from ethanol, isopropyl alcohol, n-butanol, acetone or mixtures thereof.

7. The composition of claim 5, wherein the food grade non-aqueous polar solvent is ethanol.

8. The composition of claim 5, wherein a weight to volume ratio of the *Salacia* plant parts to the food grade non-aqueous polar solvent used to obtain the extract ranges from 1:2 to 1:30.

9. A method of reducing appetite, activating hormone sensitive lipase, and/or inhibiting HMG-CoA reductase enzyme, the method comprises administering an effective amount of a *Salacia* composition to a subject in need thereof, the composition comprising at least 12% polyphenols, at least 2% mangiferin, and at least 1% 25,26-oxidofriedelane-1,3-dione by weight of the composition, wherein a daily amount of the 25,26-oxidofriedelane-1,3-dione is at least 5 mg/kg and wherein the compounds are extracted from *Salacia* plant parts, and obtained by a first extraction with a first solvent at 60° C.-65° C. for three hours, then filtration, and by a second extraction with a second solvent at 60° C.-65° C. for one hour, then filtration.

10. The method of claim 9, wherein the method maintains a healthy lipid profile by inhibition of HMG-CoA Reductase enzyme.

11. The method of claim 9, wherein the method maintains healthy lipid profile by inhibiting HMG-CoA Reductase enzyme at IC50 of not less than 400 μg/ml.

12. The method of claim 9, wherein the method reduces food intake.

13. The method of claim 9, wherein the method increases fecal fat excretion.

14. A process for preparation of novel *Salacia* composition, comprising at least 12% polyphenols, at least 2% mangiferin, and at least 1% 25,26-oxidofriedelane-1,3-dione by weight of the composition, the compounds are extracted from *Salacia* plant parts, wherein the 25,26-oxidofriedelane-1,3-dione is in a daily amount of at least 5 mg/kg, and the composition reduces appetite, activates Hormone Sensitive Lipase, and/or manages healthy lipid profile, the process comprising:

(i) Drying and grinding *Salacia* plant parts;
(ii) Stirring the plant parts of step (i) with a first food grade non-aqueous polar solvent at 60° C.-65° C. for three hours;
(iii) Filtering the food grade non-aqueous polar solvent from step (ii);
(iv) Restirring the *Salacia* plant parts with a second food grade non-aqueous polar solvent at 60° C.-65° C. for one hour;
(v) Filtering the food grade non-aqueous polar solvent from step (iv);
(vi) Combining filtrate from steps (iii) and (v) and evaporating to obtain the *Salacia* composition in the form of an extract; and
(vii) Further purifying the resulting extract by a partitioning with a food grade solvent, wherein the first and second food grade non-aqueous polar solvents of step (ii) and step (iv) and the food grade solvent of step (vii) are selected from the group consisting of ethanol, isopropyl alcohol, n-butanol, acetone, and mixtures thereof.

15. The process of claim 14, wherein the *Salacia* plant parts are selected from aerial, sub-aerial, or underground plant parts of *Salacia*, or the combinations thereof.

16. The process of claim 14, wherein the *Salacia* plant parts are selected from stems, leaves, or roots of *Salacia reticulata* and/or *Salacia oblonga*, or the combinations thereof.

17. The process of claim 14, wherein a first or second weight to volume ratio of the *Salacia* plant parts to the food grade non-aqueous polar solvent ranges from 1:2 to 1:30.

18. The process of claim 14, wherein the first or second food grade non-aqueous polar solvent is ethanol.

* * * * *